United States Patent [19]

Kumar et al.

[11] Patent Number: 5,350,875
[45] Date of Patent: Sep. 27, 1994

[54] MICHAEL REACTION

[75] Inventors: Govindarajulu Kumar; Mahmood Sabahi, both of Baton Rouge, La.

[73] Assignee: Albemarle Corporation, Richmond, Va.

[21] Appl. No.: 156,755

[22] Filed: Nov. 23, 1993

Related U.S. Application Data

[63] Continuation-in-part of Ser. No. 34,950, Mar. 22, 1993, abandoned.

[51] Int. Cl.$^5$ .............................................. C07C 69/34
[52] U.S. Cl. .................................................. 560/190
[58] Field of Search ........................ 560/190, 191, 204

[56] References Cited

U.S. PATENT DOCUMENTS 2,396,626  1/1941  Weist .................................. 260/464

*Primary Examiner*—Jose' G. Dees
*Assistant Examiner*—Samuel Barts
*Attorney, Agent, or Firm*—Richard J. Hammond

[57] ABSTRACT

Compounds varying from liquids to solids can be prepared via a reaction in which at least one Michael donor is reacted with one or more Michael acceptors in the presence of an undissolved basic compound as the catalyst.

2 Claims, No Drawings

MICHAEL REACTION

Cross-Reference to Related Application

This application is a continuation-in-part of copending application Ser. No. 08/034,950, filed Mar. 22, 1993, now abandoned.

FIELD OF INVENTION

The invention relates to Michael addition products and, more particularly, to a novel process for preparing them.

BACKGROUND

The Michael reaction is a known process wherein a Michael acceptor (such as an α,β-ethylenically-unsaturated aldehyde, ester, nitrile, ketone, sulfone, or sulfoxide) is reacted with a Michael donor (such as a dialkyl malonate) to elongate a carbon chain.

As shown by U.S. Pat. No. 2,396,626 (Wiest et al.); Skarzewski, "The Michael Reaction of Methanetricarboxylic Esters. A Simple Method for Two-Carbon Chain Elongation," Synthesis, December 1990, pp. 1125-1127; and copending application Ser. No. 07/947,628 (Sabahi et al.), such reactions have been conducted so as to form a variety of products containing one, two, three, or even more acceptor moieties per donor moiety. However, regardless of the nature of the desired product, these reactions have always been conducted by a homogeneous basic catalysis achieved by dissolving a basic compound in a reactant or by solubilizing it with the aid of a solvent or a phase transfer catalyst.

SUMMARY OF INVENTION

It has now unexpectedly been found that Michael products may be prepared by the heterogeneously catalyzed reaction of at least one Michael donor with one or more Michael acceptors at a temperature of 0°–150° C., using an undissolved basic compound as the catalyst.

DETAILED DESCRIPTION

As in Sabahi et al., the teachings of which are incorporated herein by reference, the Michael donors which can be used in the reaction include all organic compounds capable of functioning as Michael donors by virtue of containing at least one active hydrogen and at least one electron withdrawing group. There is no maximum to the number of electron withdrawing groups that may be present in the Michael donors. However, the donors usually contain 1–4 electron withdrawing groups such as —CN, —COOR, —C(O)R', —OAr, —OR, —NR$_2$, —SO$_2$R, —SO$_2$Ar, —S(O)R', —SR, —CF$_3$, —F, —Cl, —Br, and —I, in which Ar is an aryl group and R and R' generally represent aliphatic, cycloaliphatic, or alphyl groups of up to 30 carbons, although R' may represent hydrogen.

Except when it is desired to have an electron withdrawing group within an electron withdrawing group to present additional reaction sites, it is usually preferred for the R and R' aliphatic, cycloaliphatic, and alphyl groups to be groups which are at least predominantly hydrocarbyl in nature, i.e., (1) contain only carbon and hydrogen or (2) contain carbon, hydrogen and one or more other atoms but contain so few of the other atoms that the predominantly hydrocarbyl nature of the group is preserved.

The expression "predominantly hydrocarbyl group," as used herein, describes a group which contains carbon, hydrogen, and at least one other atom but in which the number of hetero atoms in a chain or ring (e.g., oxygen, sulfur, or phosphorus atoms) or non-hydrocarbyl substituents (such as alkoxy, halo, or cyano groups) is ≦0.3, preferably ≦0.1 per carbon. Since these predominantly hydrocarbyl groups can be regarded as being virtually the same as the alkyl, cycloalkyl, aralkyl, and alkenyl groups to which they most closely correspond, terms such as "alkyl" are sometimes used herein to include the predominantly hydrocarbyl groups as well as the hydrocarbyl groups normally denoted by those terms.

Utilizable Michael donors include compounds such as N,N-dimethylaminoethane, N,N'-dimethyldiaminomethane, N,N,N',N'-tetraethyldiaminomethane, diethylsulfone, dipropylsulfone, ethyl phenyl sulfone, dimethylsulfoxide, difluoromethane, dichloromethane, 1,1-dibromoethane, 1,1-diiodopropane, 1,1,1-trifluoroethane, diphenoxymethane, diethoxymethane, methyl vinyl ketone, ethyl vinyl ketone, propyl vinyl ketone, 1,3-cyclohexanedione, 1,4-dicyclohexanedione, 1-methoxypropanethiol, diethylthiomethane, didodecyl malonate, dibenzyl malonate, octadecyl propionate, methyl p-fluorophenoxyacetate, ethyl p-chlorophenylacetate, and methoxypropyl acetate. However, the more preferred donors are those in which the electron withdrawing groups are —COOR, —C(O)R', and/or —CN groups wherein R and R' are alkyl or cycloalkyl groups of up to 10 carbons, most preferably methyl or ethyl.

Exemplary of these more preferred donors are (1) the methyl, ethyl, propyl, isopropyl, butyl, isobutyl, t-butyl, pentyl, hexyl, chlorohexyl, heptyl, octyl, decyl, bromodecyl, ethoxyoctyl, cyclopropyl, cyclopentyl, cyclohexyl, and cyclooctyl esters of (cyclo)alkanoic and substituted (cyclo)alkanoic acids such as acetic, chloroacetic, cyanoacetic, propionic, butyric, bromobutyric, cyclobutanecarboxylic, cyclohexanecarboxylic, and cycloheptane carboxylic acids, (2) the corresponding diesters of 1,1-dicarboxy(cyclo)alkanes and other dicarboxy(cyclo)alkanes (e.g., succinic, glutaric, and higher acids of the oxalic acid series, and 1,4-cyclohexanedicarboxylic acid) in which the (cyclo)alkane moiety is a divalent hydrocarbylene radical derived from a (cyclo)alkane such as methane, ethane, propane, isopropane, butane, isobutane, t-butane, pentane, hexane, heptane, octane, propoxypentane, butoxypentane, nonane, decane, ethoxyoctane, undecane, cyclopentane, cyclohexane, cycloheptane, or cyclooctane; (3) the corresponding diesters of 1,1-dicarboxy-1-cycloalkylmethanes in which the cycloalkyl substituent is cyclopropyl, cyclopentyl, cyclohexyl, or cyclooctyl; (4) the corresponding dicyano- and diacyl-substituted (cyclo)alkanes and cycloalkylmethanes in which the acyl groups are acetyl, propionyl, butyryl, or isobutyryl; and (5) the corresponding cyano- or acyl-substituted (cyclo)alkanoic and cycloalkylethanoic acid esters.

In a preferred embodiment of the invention, the Michael donors employed in the process are Z'—CH(E)(E") compounds wherein Z' is hydrogen or an alkyl or cycloalkyl group of up to 10 carbons, E" is hydrogen or an electron withdrawing group, and E is an electron withdrawing group—the electron withdrawing group or groups being any of those mentioned above but preferably being —COOR, —C(O)R', and/or —CN groups in which R and R' are alkyl or cycloalkyl groups of up to 10 carbons, preferably methyl or ethyl. The most preferred Michael donors are the dimethyl and diethyl malonates; the methyl and ethyl cyanoacetates, chloroacetates, acetoacetates, and propionylacetates; malononitrile; acetonitrile; acetylacetone; and dipropionylmethane.

Michael acceptors which can be reacted with these Michael donors include all organic compounds capable of functioning as Michael acceptors by virtue of containing a double bond activated by at least one electron withdrawing group, although the more reactive acceptors are apt to be preferred. Like the Michael donors, the Michael acceptors may have the one or more electron withdrawing groups attached to aliphatic or cycloaliphatic carbons, may contain electron withdrawing groups within electron withdrawing groups, and most commonly contain electron withdrawing groups selected from —CN, —COOR, —C(O)R', —OAr, —OR, —NR$_2$, —SO$_2$R, —SO$_2$Ar, —S(O)R', —SR, —CF$_3$, —F, —Cl, —Br, and —I, in which Ar, R, and R' have the definitions given above. Moreover, the unsaturated aliphatic and cycloaliphatic compounds bearing these electron withdrawing groups may be otherwise hydrocarbyl, predominantly hydrocarbyl, or non-hydrocarbyl in nature.

Utilizable Michael acceptors include compounds such as methyl vinyl sulfone, vinyl o-tolyl sulfone, p-tolyl styryl sulfone, the vinyl and vinylidene halides, methyl vinyl ether, ethyl vinyl ether, phenyl vinyl ether, methyl vinyl sulfide, ethyl vinyl sulfide, and 1-cyanocyclohexene. However, the more preferred acceptors are compounds such as (1) the methyl, ethyl, propyl, isopropyl, butyl, isobutyl, t-butyl, pentyl, hexyl, chlorohexyl, heptyl, octyl, decyl, bromodecyl, ethoxyoctyl, ethylthiononyl, dodecyl, cyanododecyl, tetradecyl, hexadecyl, octadecyl, eicosyl, cyclopropyl, cyclopentyl, cyclohexyl, and cyclooctyl esters of acrylic, methacrylic, ethacrylic, crotonic, and cinnamic acids, (2) the corresponding esters of 1-carboxy-1-cyanoethylene and corresponding diesters of 1,1-dicarboxy-2-cyanoethylene and 1,1-dicarboxyethylene, (3) nitriles such as acrylonitrile, methacrylonitrile, ethacrylonitrile, dicyanoethylene, and tricyanoethylene, (4) aldehydes such as acrolein, methacrolein, ethacrolein, crotonaldehyde, and cinnamaldehyde, and (5) ketones such as methyl vinyl ketone and ethyl vinyl ketone.

In the preferred embodiment of the invention utilizing Z'-CH(E)(E'') compounds as Michael donors, the preferred Michael acceptors are ordinarily CTT'=CT''G compounds in which T, T', and T'' are independently selected from hydrogen, G', and organic groups (e.g., alkyl, alkoxyalkyl, alkylthioalkyl, cycloalkyl, dialkylaminocycloalkyl, aryl, haloaryl, alkoxyaryl, aralkyl, and alkaryl groups) of up to 20 carbons; and G and G' are electron withdrawing groups—the electron withdrawing group or groups being any of those mentioned above but preferably being —COOR, —C(O)R', and/or —CN groups in which R and R' are alkyl or cycloalkyl groups of up to 20 carbons.

Of these preferred compounds, the Michael acceptors which are apt to be most preferred are (A) those in which T, T', and T'' are hydrogen and G is a —CN, —COOR, or —C(O)R' group wherein R and R' are methyl or ethyl and (B) the corresponding compounds in which one or two of the hydrogens represented by T, T', and T'' is replaced with a G' electron withdrawing group which may be the same as G or a different group selected from —CN, —COOR, and C(O)R'. The especially preferred Michael acceptors are the methyl and ethyl acrylates, acrylonitrile, dicyanoethylene, tricyanoethylene, methyl vinyl ketone, and ethyl vinyl ketone.

Using the preferred Michael donors and acceptors disclosed above permits the formation of compounds corresponding to the formula Z—C(E)(E')$_p$—Q$_s$ in which Z is alkyl, cycloalkyl, or —(CTT'—CT''G-)$_w$—CTT'—CHT''G; Q is —(CTT'—CT''G)$_t$—CTT'—CHT''G; E' is an electron withdrawing group; T, T', T'', E and G have the definitions given above; p is zero or one; s is respectively two or one; and each of t and w represents zero or a positive integer such that the compound contains at least one, preferably 1–10 G groups. The most preferred of these compounds are:

(A) those in which p and s are one; Z is —(CTT'—CT''G)$_w$—CTT'—CHT''G; E, E', G, and G' are independently selected from —CN, —COOR, and —C(O)R' groups wherein R and R' represent aliphatic, cycloaliphatic, or alphyl groups containing up to 30 carbons, usually alkyl or cycloalkyl groups containing up to 10 carbons; and the sum of t and w is 0–10 and (B) those in which s is two; Z is —(CTT'—CT''G)$_w$—CTT'—CHT''G; E, G, and G' are independently selected from —CN, —COOR, and —C(O)R' groups wherein R and R' represent aliphatic, cycloaliphatic, or alphyl groups containing up to 30 carbons, usually alkyl or cycloalkyl groups containing up to 10 carbons; and the sum of t and w is 0–10.

The reaction between the Michael donor and Michael acceptor is conducted in the presence of an undissolved basic compound at a suitable temperature, usually a temperature of about 0°–150° C., preferably about 20°–120° C., and most preferably about 60°–110° C.

Although the basic compound, which serves to initiate the reaction, may be any other suitable base, it is preferably a solid alkali or alkaline earth metal hydroxide, alkoxide, or carbonate, more preferably a sodium or potassium hydroxide, alkoxide, or carbonate, and most preferably sodium or potassium carbonate. It may be used in any catalytic amount sufficient to initiate the reaction and, surprisingly, does not have to be employed in a concentration higher than that utilized in the process of Sabahi et al.—a process which also benefits from the use of a phase transfer catalyst which solubilizes the basic compound and was formerly believed to be an essential component of the reaction mixture. Thus, as in Sabahi et al., the basic compound is utilized in a sub-stoichiometric concentration which is usually about 1–50%, preferably 3–30%, and most preferably 5–10%, based on the weight of the Michael donor.

The Michael reaction of the invention is usually conducted in the absence of a solvent, but it may sometimes be desirable to increase the efficiency of the reaction by utilizing a diluent which serves as a solvent for the reactants but does not dissolve the basic compound. When used, the solvent should be a non-nucleophilic substance, e.g., a hydrocarbon, which will maintain the reactants in solution during the reaction but permit easy separation of the products from the reaction mixture. Such solvents include, e.g., toluene, xylene, other alkylbenzenes, hexane, and other saturated hydrocarbons.

The reaction is effected by combining the reactants and initiator, optionally in the presence of a solvent, and maintaining contact between the reactants at the selected reaction temperature until the desired degree of reaction has been effected.

Regardless of the acceptor/donor ratio in the reaction mixture, the reaction normally leads to the formation of a mixture of products containing different numbers of acceptor moieties per molecule—including products containing more acceptor moieties than the number that would theoretically be provided by the amount of acceptor employed in the reaction. These product mixtures most commonly contain a preponderant amount of molecules containing 1–2 acceptor moieties/donor moiety. However, the number of molecules containing more than two acceptor moieties/donor moiety can be increased by the use of (1) the higher reaction temperatures, (2) the larger amounts of basic compound, (3) the stronger basic compounds, (4) reactants containing the stronger electron withdrawing groups, and (5) reaction mixtures in which the acceptor/donor tool ratio is at least 3/1, e.g., 3–30/1.

Variations in product structure and properties can be achieved by using mixtures of donor compounds and/or mixtures of acceptor compounds in the reaction.

After completion of the reaction to form a mixture of compounds containing different numbers of acceptor moieties per molecule, (1) the product may be fractionated into individual components or groups of components and/or (2) it may be subjected to one or more additional reactions, such as transesterification, prior to being used in the desired application. However, the product mixtures themselves are also useful materials, so fractionations of the products are frequently unnecessary; and post-treatments of the products, e.g., by transesterification, are used only when the product of the Michael reaction does not have the properties desired for its end use but can acquire those properties by such a post-treatment.

The products resulting from the Michael reaction or from conversion of the Michael reaction products to derivatives are typically washed with water to remove any unreacted materials and basic compound prior to being used in their intended application; and, if desired, they may then be further purified by subjecting them to fractional distillation. They may then be utilized alone or together with other materials serving similar functions and/or with additives serving other functions in their intended application, e.g., as plasticizers, solvents, lubricants, molding materials, or any of the other uses mentioned above.

The invention is advantageous in that its use of an undissolved catalyst permits easy removal of the catalyst from the product by filtration and—in the case of reactions conducted to form Michael products containing $\geq 3$ acceptor moieties/donor moiety (reactions in which polymerization of the acceptor can be a serious problem when homogeneous catalysis is employed)—minimizes polymerization of the acceptor.

The following examples are given to illustrate the invention and are not intended as a limitation thereof.

EXAMPLE 1

Charge a reaction vessel with 13.2 g (0.1 mol) of dimethyl malonate and 0.15 g (0.001 mol) of potassium carbonate, heat the mixture to 35° C., and slowly add 43.0 g (0.5 mol) of methyl acrylate so as to keep the temperature below 60° C. After completing the addition of the acrylate, reflux the reaction mixture for four hours. Analysis shows the product to consist, in area percentages, of 86.7% tetramethyl ester of 1,3,3,5-pentanetetracarboxylic acid, 9.5% pentamethyl ester of 1,3,3,5,7-heptanepentacarboxylic acid, 2.6% hexamethyl ester of 1,3,5,5,7,9-nonanehexacarboxylic acid, and 1.2% higher esters, i.e., products having more than six ester groups per molecule.

EXAMPLE 2

Repeat Example 1 except for replacing the potassium carbonate with 0.01 mol of sodium carbonate and conducting the reaction at 80°–100° C. After four hours the product consists of 54% trimethyl ester of 1,1,3-propanetricarboxylic acid, 44% tetramethyl ester of 1,3,3,5-pentanetetracarboxylic acid, and 2% higher esters, i.e., products having more than four ester groups per molecule.

EXAMPLE 3

Charge 12.9 g (0.15 mol) of methyl acrylate over a period of five minutes to a reaction vessel containing a stirred mixture of 6.6 g (0.05 mol) of dimethyl malonate and 0.28 g (0.005 mol) of potassium hydroxide maintained at room temperature under nitrogen. The addition results in a rapid increase in the temperature. After ten minutes, GC analysis shows the product to consist of >95% tetramethyl ester of 1,3,3,5-pentanetetracarboxylic acid and <5% heavier esters.

What is claimed is:

1. A process which comprises reacting in the presence of an undissolved basic compound as a catalyst at least one Michael donor corresponding to the formula $Z'$—CH(E)(E'') in which $Z'$ is hydrogen, alkyl, or cycloalkyl and $E''$ is hydrogen or an electron withdrawing group is reacted with at least one Michael acceptor corresponding to the formula $CTT'=CT''G$ to form product molecules corresponding to the formula Z—C (E) (E')$_p$—Q$_s$ in which Z is alkyl, cycloalkyl, or —(CT'—CT''G)$_w$—CTT'—CHT''G; Q is —(CTT'—CT''G-)$_t$—CTT'—CHT''G; p is zero or one; s is respectively two or one; and each of t and w represents zero or a positive integer such that the compound contains at least acceptor moiety—T, T' and T'' in the above formulas being independently selected from hydrogen, G', and organic groups of up to 20 carbons; and E, E', G, and G' being independently selected from electron withdrawing groups.

2. The process of claim 1, wherein $Z'$ is hydrogen, E and $E''$ are —COOR groups, $CTT'=CT'G$ is $CH_2=CHCOOR$, and the product molecules correspond to the formula ROOCCH$_2$CH$_2$—(-ROOCCHCH$_2$)$_w$—C(COOR)$_2$—(CH$_2$CHCOOR)-$_t$—CH$_2$CH$_2$COOR in which the sum of t and w in the molecules is in the range of 0–10 and the —COOR groups are independently selected from —COOR groups in which R is an alkyl of 1–8 carbons.

* * * * *